(12) United States Patent
Penhasi

(10) Patent No.: US 11,039,637 B2
(45) Date of Patent: Jun. 22, 2021

(54) COMPOSITION AND METHOD FOR IMPROVING STABILITY AND EXTENDING SHELF LIFE OF PROBIOTIC BACTERIA AND FOOD PRODUCTS THEREOF

(71) Applicant: Adel Penhasi, Holon (IL)

(72) Inventor: Adel Penhasi, Holon (IL)

(73) Assignee: DeGama Berrier Ltd., Grand Cayman (KY)

( * ) Notice: Subject to any disclaimer, the term of this patent is extended or adjusted under 35 U.S.C. 154(b) by 0 days.

(21) Appl. No.: 15/246,941

(22) Filed: Aug. 25, 2016

(65) Prior Publication Data

US 2016/0360777 A1  Dec. 15, 2016

Related U.S. Application Data

(63) Continuation of application No. 13/991,911, filed as application No. PCT/IB2011/055462 on Dec. 5, 2011, now abandoned.

(60) Provisional application No. 61/419,885, filed on Dec. 6, 2010.

(51) Int. Cl.

| | |
|---|---|
| A23L 33/135 | (2016.01) |
| A61K 9/48 | (2006.01) |
| A61K 9/50 | (2006.01) |
| A61K 35/745 | (2015.01) |
| A21D 8/04 | (2006.01) |
| A23P 10/35 | (2016.01) |
| A23P 10/30 | (2016.01) |
| C12N 1/04 | (2006.01) |
| A61K 35/00 | (2006.01) |

(52) U.S. Cl.
CPC ............ *A23L 33/135* (2016.08); *A21D 8/045* (2013.01); *A23P 10/30* (2016.08); *A23P 10/35* (2016.08); *A61K 9/4858* (2013.01); *A61K 9/5015* (2013.01); *A61K 9/5031* (2013.01); *A61K 9/5036* (2013.01); *A61K 9/5042* (2013.01); *A61K 9/5073* (2013.01); *A61K 35/745* (2013.01); *C12N 1/04* (2013.01); *A23V 2002/00* (2013.01); *A61K 2035/115* (2013.01)

(58) Field of Classification Search
CPC ... A23L 33/135; A61K 35/745; A61K 9/4858; A61K 9/5015; A61K 9/5031; A61K 9/5036; A61K 9/5042
USPC .......................................................... 426/61
See application file for complete search history.

(56) References Cited

U.S. PATENT DOCUMENTS

| | | | |
|---|---|---|---|
| 4,515,769 A | 5/1985 | Merritt et al. | |
| 4,994,279 A | 2/1991 | Aoki et al. | |
| 6,234,464 B1 | 5/2001 | Krumbholz et al. | |
| 6,974,594 B2 | 12/2005 | Ko et al. | |
| 7,157,258 B2 | 1/2007 | Durand et al. | |
| 2003/0012819 A1 | 1/2003 | Ko et al. | |
| 2004/0121002 A1 | 6/2004 | Lee et al. | |
| 2004/0175389 A1 | 9/2004 | Porubcan | |
| 2005/0008610 A1 | 1/2005 | Schwarz et al. | |
| 2005/0019417 A1 | 1/2005 | Ko et al. | |
| 2005/0153018 A1 | 7/2005 | Ubbink et al. | |
| 2005/0266069 A1* | 12/2005 | Simmons | A23L 33/135 424/451 |
| 2006/0029646 A1 | 2/2006 | Vanderkooi | |
| 2006/0034937 A1 | 2/2006 | Patel | |
| 2007/0098847 A1 | 5/2007 | Teissier | |
| 2007/0098854 A1 | 5/2007 | Van Lengerich et al. | |
| 2007/0160589 A1 | 7/2007 | Mattson et al. | |
| 2008/0193485 A1 | 8/2008 | Gorbach et al. | |
| 2009/0092704 A1* | 4/2009 | Gately | A23K 40/35 426/2 |
| 2009/0214647 A1 | 8/2009 | Chen | |
| 2010/0047400 A1 | 2/2010 | Carlson et al. | |
| 2010/0055083 A1 | 3/2010 | Kowalski et al. | |
| 2010/0074994 A1 | 3/2010 | Harel et al. | |
| 2010/0076045 A1* | 3/2010 | Castillo | A61K 9/0048 514/407 |

(Continued)

FOREIGN PATENT DOCUMENTS

| | | |
|---|---|---|
| CA | 2730066 | 1/2010 |
| CA | 2735659 | 3/2010 |

(Continued)

OTHER PUBLICATIONS

Ubbink, J. et al. Trends in Food Sci. Technol. 17:244-254 (2006).*

(Continued)

*Primary Examiner* — Hamid R Badr
(74) *Attorney, Agent, or Firm* — Alphapatent Associates, Ltd; Daniel J. Swirsky

(57) ABSTRACT

A composition comprising probiotic bacteria, the composition comprising: (a) a core composition containing the probiotic bacteria and a stabilizer, wherein the total amount of probiotics in the mixture is from about 10% to about 90% by weight of the core composition; (b) an innermost coating layer, layered on said core composition, comprising at least one hydrophobic solid fat or fatty acid having a melting point lower than 60° C.; (c) an intermediate coating layer layered on said innermost coating layer, which when present in an aqueous solution in the amount of 0.1% weight/weight over the weight of the solution, has a surface tension lower than 60 mN/m, when measured at 25° C.; and (d) an outer coating layer, layered on said intermediate coating layer; wherein the composition is in the form of particles; food products containing the composition and methods of preparation thereof.

14 Claims, 3 Drawing Sheets

(56) References Cited

U.S. PATENT DOCUMENTS

| | | |
|---|---|---|
| 2010/0189767 A1 | 7/2010 | Shimoni et al. |
| 2010/0303962 A1 | 12/2010 | Penhasi |
| 2011/0008493 A1 | 1/2011 | Zorea |

FOREIGN PATENT DOCUMENTS

| | | |
|---|---|---|
| CN | 1613455 | 5/2005 |
| EP | 0937496 | 8/1999 |
| EP | 1010372 A2 | 6/2000 |
| EP | 1110462 A3 | 6/2001 |
| EP | 1382241 | 1/2004 |
| KR | 940 004 883 | 3/1994 |
| WO | 199400019 A1 | 1/1994 |
| WO | 199608261 A1 | 3/1996 |
| WO | 0074499 | 12/2000 |
| WO | 2004022031 A2 | 3/2004 |
| WO | 2007058614 A1 | 5/2007 |
| WO | 2007100179 A1 | 9/2007 |
| WO | 2008035332 A1 | 3/2008 |
| WO | 2008037578 A1 | 4/2008 |
| WO | 2009069122 A1 | 6/2009 |
| WO | 2009089115 A1 | 7/2009 |
| WO | 2009158368 A1 | 12/2009 |
| WO | 2011004375 | 1/2011 |
| WO | 2011004375 A1 | 1/2011 |
| WO | 2012020403 A1 | 2/2012 |

OTHER PUBLICATIONS

Trademark Basics: A Guide for Business. International Trademark Association (INTA) (Year: 2012).*
Office action for the corresponding European patent application No. 11815718.9, dated Jun. 17, 2015.
Hercules, Inc., Aqualon Sodium Carboxymethylcellulose Physical and Chemical Properties, 1999.
Ashland, Product Grades Available, 2017.
Krasaekoopt et al. Evaluation of encapsulation techniques of probiotics for yoghurt. Int Dairy J 2003; vol. 13, pp. 3-13.
Fathi Azarbayjani et al. Impact of surface tension in pharmaceutical sciences. J Pharm. Pharma Sci 2009; vol. 12, 218-228.
Ubbink et al. Trends in Food Science and Technology. 2006. 17:244-254.
Krasaekoopt W et al., "The influence of coating materials on some properties of alginate beads and the survivability of microencapsulated probiotic bacteria", International Dairy Journal,14I8, pp. 737-743, Aug. 2004.
Pegg RB et al., "Chapter 22: Encapsulation, stabilization, and controlled release of food ingredients and bioactives", Handbook of Food Preservation 2nd Edition, Rahman MS, CRC Press, Boca Raton, 2007, pp. 509-568.
International search report for related PCTIL 1100640 dated Dec. 23, 2011.
Examination report for related AU 2010269814 dated Jan. 16, 2013.
Examination report for related NZ 597992 dated Jul. 23, 2012.
IPR for PCT/IL2008/001539 mailed Jun. 1, 2010.
ISR for PCT/IL2010/00550 mailed Nov. 12, 2010.
OA for related CN 201080035882.5 mailed Jan. 5, 2013.
Extended SR for EP 10796812.5 mailed Jul. 16, 2013.
Anal et al. Recent advances in microencapsulation of probiotics for industrial applications and targeted delivery. Trends in Food Science & Technology vol. 18, Issue 5, pp. 240-251. May 2007.
International Search Report for related PCT/IL2012/050533 dated May 12, 2013.
Madene et al. Flavor encapsulation and controlled release—a review. International Journal of Food Science& Technology. 41.1 (2006): 1-21.
Yoshii et al. Flavor release from spray-dried maltodextrin/gum arabic or soy matrices as a function of storage relative humidity. Innovative Food Science & Emerging Technologies 2.1 (2001): 55-61.
International Search Report for related PCT/IB2011/055462 dated May 2, 2012.
Database WPI 1-61 Week 199611 Thompson Scientific, London, GB; AN 1996-103950 XP002672415, & KR 940 004 883 B1 (Hill Glucose co LTD) Jun. 4, 1994 (Jun. 4, 1994).
Office Action for related CN201180065438 Translation dated Jun. 18, 2014.
International Search Report for related PCT/IL2012/050453 dated May 10, 2013.
Evonik: Technical information EUDRAGIT L30 D-55, Jan. 1, 2012, XP55040439, retrieved from the internet: URL: http://eudragit.evonik.com/product/eudragit/Documents/evonik-specifications-eudragit-I-30-d-55.pdf [retrieved on Oct. 9, 2012].
Fmc biopolymer: Material Safety Data Sheet Aquacoat CPD cellulose Acetate Phthalate Aqueous Dispersion; Jan. 1, 2006, XP55040437, retrieved from the internet: URL: http://www.fmcbiopolymer.com/Portals/Pharm/Content/Docs/aquacoatcpdmsds.pdf [retrieved on Oct. 9, 2012].
Dow Chemicals: ETHOCEL: Ethylcellulose Polymers Technical Handbook. Sep. 1, 2005, XP55040326, retrieved from the Internet: URL: http://www.dow.com/dowwolff/en/pdf/192-00818.pdf [retrieved on Oct. 8, 2012].
Colorcon: Opadry II, Opadry amb, Aug. 1, 2009, XP55040271, retrieved from the internet: URL: http://www.colorcon.com/literature/marketing/fc/Opadry II/ads_opadry_II_amb_IRfc_matracices.pdf [retrieved on Oct. 8, 2012].
Seppic: Sepifilm LP, Sep. 1, 2004, XP55040273, etrieved from the internet: URL: http://abstracts.aapspharmaceutica.com/expoaaps07/Data/EC/Event/Exhibitors/202/2e4a0b37-9255-47c1-8b7f-ffe724b25ee1.pdf [retrieved on Oct. 8, 2012].
International Search Report for related PCT/IB2012/052857 dated Oct. 15, 2012.
International Search Report for related PCT/IL2014/050368 dated Aug. 25, 2014.
Office Action for related IL 187645 dated May 23, 2011.
Chen et al. Optimal combination of the encapsulating materials for probiotic microcapsules and its experimental verification (R1). J Food Engineering 2006; vol. 76, pp. 313-320.
Zuidam et al. Overview of microencapsulates for use in food products or processes and methods to make them. Encapsulation Technologies for Active Food Ingredients and Food Processing; Springer 2010; 1st ed. chapter 2, 3-29.
Kurtmann et al. Storage stability of freeze-dried Lactobacillus acidophilus (La-5) in relation to water activity and presence of oxygen and ascorbate. Cryobiol. 2009; vol. 58, pp. 175-180.
Mazeaud, Danisco Cultures Innovation. Encapsulation of Probiotics for Food Applications. Industrial workshop on microencapsulation of flavors and bioactives for functional food applications. Minneapolis Airport Marriott, Bloomington, Minnesota. Sep. 14-15, 2009.
Aulton M. Surface effects in film coating. ed. by Taylor & Francis 1995; Chapter 5; 118-151. ISBN 0-13-662-891-5.
CA2820178—Office Action dated Jan. 2, 2018.
CA2820178—Amendment dated Jul. 3, 2018.
CA2820178—Office Action dated Dec. 27, 2018.
CA2820178—Amendment dated Jun. 25, 2020.
Manojlovic et al., Encapsulation Technologies for Active Food Ingredients and Food Processing, Jan. 1, 2010, Springer, pp. 272-302.
Mazeaud, Danisco Cultures Innovation. Encapsulation of Probiotics for Food Applications. Industrial Workshop on Microencapsulation of Flavors and Bioactives for Functional Food Applications. Minneapolis Airport Marriott, Bloomington, Minnesota, USA. Sep. 14-15, 2009.
EP2648528—Notice of Opposition dated Apr. 20, 2017.
EP2648528—Notice to File Observations dated May 3, 2017.
EP2648528—Reply to Notice to File Observations dated Nov. 30, 2017.
EP2648528—Annex to Summons dated Apr. 11, 2018.
EP2648528—Written Submission by Patent Holder dated Sep. 14, 2018.
EP2648528—Written Submission by Opponent dated Sep. 14, 2018.
EP2648528—Annex Communication dated Nov. 15, 2018.

(56) References Cited

OTHER PUBLICATIONS

EP2648528—Oral Proceedings, Minutes, and Decision dated Dec. 6, 2018.
EP2648528—Notice of Appeal dated Feb. 6, 2019.
EP2648528—Grounds for Appeal dated Apr. 15, 2019.
EP2648528—Reply to Notice of Appeal dated Aug. 13, 2019.
WO2012077038—IPRP dated Jun. 12, 2013.
PCTIL2008001539—IPRP dated Jun. 1, 2010.

\* cited by examiner

COMPOSITION AND METHOD FOR IMPROVING STABILITY AND EXTENDING SHELF LIFE OF PROBIOTIC BACTERIA AND FOOD PRODUCTS THEREOF

FIELD OF THE INVENTION

The present invention relates generally to probiotics and food products containing such and in particular, but not exclusively, to compositions containing stabilized probiotics with improved stability and extended shelf life.

BACKGROUND OF THE INVENTION

Probiotics are live microbial food supplements which beneficially affect the host by supporting naturally occurring gut flora, by competing harmful microorganisms in the gastrointestinal tract, by assisting useful metabolic processes, and by strengthening the resistance of the host organism against toxic substances. The beneficial effects that probiotics may induce are numerous. Some non-limiting examples include the reduction of lactose intolerance, the inhibition of pathogenic bacteria and parasites, the reduction of diarrhea, activity against *Helicobacter pylori*, the prevention of colon cancer, the improvement or prevention of constipation, the in situ production of vitamins, the modulation of blood fats, and the modulation of host immune functions. In domesticated and aquatic animals they also can improve growth, survival and stress resistance associated with diseases and unfavorable culture conditions. Therefore, there is considerable interest in including probiotics into human foodstuffs and into animal feed.

Probiotic organisms are preferably alive and capable of activity until and including during ingestion, in order to be effective. Probiotic organisms are usually incorporated into milk products, such as yogurts, which provide some inherent stability and which do not require heat for processing. However, it is difficult to incorporate the beneficial microorganisms in other foodstuff types, for example creams, biscuits fill-in, chocolate, sauces, mayonnaise and etc., especially those which optionally undergo heat treatment in at least one stage of their preparation. Heat treatment is known to decrease viability of probiotic organisms and, if sufficiently high or applied for a sufficiently long period of time, will kill these organisms.

The activity and long term stability of probiotic bacteria may be affected by a number of environmental factors; for example, temperature, pH, the presence of water/humidity and oxygen or oxidizing or reducing agents. It is well known that, in an aqueous phase, probiotics instantly lose their activity during storage at ambient temperatures (AT). Generally, probiotic bacteria are dried before or during mixing with other foodstuff ingredients. The drying process can often result in a significant loss in activity from mechanical, chemical, and osmotic stresses induced by the drying process. Loss of activity may occur at many different stages, including drying during initial manufacturing, food preparation (upon exposure to high temperature, high humidity, oxygen and high pressure), transportation and long term storage (temperature, oxygen and humid exposure), and after consumption and passage in the gastrointestinal (GI) track (exposure to low pH, proteolytic enzymes and bile salts). Manufacturing food or feedstuffs with live cell organisms or probiotics is in particular challenging, because the probiotics are very sensitive to oxygen, temperature and moisture, all of which are typically present in the foodstuff itself and/or its manufacture.

Many probiotics exhibit their beneficial effect mainly when they are alive. Hence, they need to survive the manufacturing process and shelf life of the food. Likewise, upon consumption of the food, they should survive adverse gastro-intestinal tract conditions, such as very low pH values present in the stomach, before reaching the proper location in the intestine for colonization. Although many commercial probiotic products are available for animal and human consumptions, most of them lose their viability during the manufacture process, transport, storage and in the animal/human GI tract.

To compensate for such loss, an excessive quantity of probiotics is included in the product, in anticipation that a portion will survive and reach their target. In addition to the questionable shelf-life viability of these products, such practices are certainly not cost-effective. Furthermore, such practices may also lead to highly variable dosages of probiotic bacteria that actually reach their intended destination for colonization, which is also undesirable.

For protection of the bacteria, various formulations have been devised, frequently incorporating protective agents such as proteins, certain polymers, skim milk, glycerol, polysaccharides, oligosaccharides and disaccharides, and the like. However, none of these formulations are able to protect properly against oxygen and moisture, nor are they able to provide suitable protection against high temperatures required for processing many foodstuffs.

For example, the probiotic microorganisms can be encapsulated by enteric coating techniques involve applying a film forming substance, usually by spraying liquids containing enteric polymer and generally other additives such as sugars or proteins onto the dry probiotics (Ko and Ping WO 02/058735). However, the enteric polymers film coating the probiotics during the microencapsulation process usually cannot function as a moisture protecting barrier and generally several layers must be added, to avoid water entering the microcapsules. In addition, such polymers also cannot provide an appropriate protection against oxygen upon very poor oxygen occlusion properties of such polymers.

Giffard and Kendall (US 2005/0079244) disclose a foodstuff in the form of a dried or semi-moist ready-to-eat kibble or powder mix, which contains a combination of a probiotic, prebiotic and a coating of colostrum. Prior to mixing in the food stuff, the probiotic is coated or encapsulated in a polysaccharide, fat, starch, protein or in a sugar matrix using standard encapsulation techniques. Similar to the above disclosure, neither the encapsulating polymers nor the additives used in both core and coating layers have low water vapor and oxygen transmission, and therefore the negative effects of water (humidity) and oxygen cannot be avoided.

Accordingly, it has been proposed to dry sugar-based probiotic systems by foam formation in a very thin layer (Bronshtein WO2005117962), or to use combinations of sugars with a polymeric gelling agent, such as alginate, chitosan, carboxymethylcellulose or carboxyethylcellulose. Cavadini et al. (EP 0 862 863) provide a cereal product comprising a gelatinized starch matrix including a coating or a filling. The probiotic is included with the coating. According to that process, spray-dried probiotics are mixed with a carrier substrate, which may be water, fat or a protein digest. The mixture is then sprayed onto the cereal product and the whole product is dried again. Re-hydrating of the already dried bacteria and the additional coating/drying process is costly and damaging to the bacteria.

US 2005/0019417 A1 describes a method of preparing products containing moisture-sensitive living microorganisms including probiotics, comprising at least the steps through which a suspension of probiotics and a sugar polymer in water miscible solvent is sprayed onto a water soluble, gel-forming solid particles. By these means, the core composed of water soluble gel-forming solid particles may absorb solvent residues and provide protection to probiotics placed onto said core.

Kenneth and Liegh (U.S. Pat. No. 6,900,173) describe the manufacturing of multivitamin protein and probiotic bar for promoting an anabolic state in a person. The dried probiotic bacteria are blended in sugar syrup and several other constituents, and the resultant mixture is then extruded and cut into bars. However, the document does not disclose any process or composition that will improve viability or long-term stability of probiotics in the nutritional bars and there is no indication that the bacteria even survive the process.

US 2004/0175389 (Porubcan) discloses a formulation for protecting probiotic bacteria during passage through the stomach, whilst permitting their release in the intestine. The formulation has also a low water activity and correspondingly long shelf life. The capsule includes a water-free mixture of probiotic bacteria with monovalent alginate salts, and an enteric coating (e.g., gelatin or cellulose encapsulation). Upon contact with acidic environment, the outer shell of the capsule turned into a gel, which provides a protecting barrier against proton influx into the capsule core. However, this composition is only useful for tablets and capsules subjected to storage conditions of very low water activity and further require storage in nitrogen-flushed or vacuum-sealed containers.

WO 03/088755 (Farber and Farber) describes an oral delivery system for functional ingredients uniformly dispersed in a matrix. The matrix components include a sugar, a carbohydrate, a hydrocolloid, a polyhydric alcohol and a source of mono- or divalent cations. The delivery system is extruded or molded into a final shape with a moisture content of between 15% and 30% by weight. This type of matrix provides very little protection to the probiotics; the little protection that is provided requires refrigerated conditions, which are not suitable or desirable for many foodstuffs. No description or direction was provided as to how probiotic bacteria are stabilized during manufacturing or for prolonged storage at room temperatures.

McGrath and Mchale (EP 1382241) describe a method of delivering a microorganism to an animal. The micro-organism is suspended in a matrix of cross-linked alginate and cryopreservant (trehalose or lactose, or a combination of both). The matrix is then freeze or vacuum dried to form dry beads containing live probiotics with a shelf-life stability up to 6 months but only under refrigerated conditions. Here again, no description or direction was provided as to how probiotic bacteria are stabilized during manufacturing or for prolonged storage at room temperatures and high humidity conditions.

Ubbink et al. (US 2005/0153018) disclose the preservation of lactic acid bacteria in moist food. The spray-dried bacteria are added to a composition comprising fats, fermented milk powder and saccharides. That composition is then used as the filling of a confectionary product. The subject matter described in that document avoids the detrimental effects of water by embedding the probiotics in fat or oil rich matrix. However, fat based coating and preserving materials alone do not withstand oxygen and long term exposure to humid conditions.

None of the above compositions provide a mixture that can effectively protect the probiotic in both drying processes and long-term storage at ambient temperatures and varying degrees of humidity. In addition, none of the above compositions provide a mixture that can effectively protect the probiotics against oxygen which is a main cause for poor stability for long time in storage conditions causing very limited shelf life.

BRIEF SUMMARY OF THE INVENTION

Many probiotics may be temperature, water and/or oxygen sensitive and thus suffer from lack of an extended shelf life. Therefore, they need protection during processing, transporting and storage as well as during delivery to the gastro intestinal tract to maintain viability.

Therefore, there is an urgent need for a composition that can effectively protect the probiotic bacteria during manufacturing, long-term storage at ambient temperature, humidity and oxygen and during gastrointestinal passage. There is a need also for a preparation process that is cost-effective and capable of entrapping and stabilizing probiotics in the protective mixture with minimal viability loss at the end of the entire operation. There is a need for a protective mixture that provides protection in the stomach while allowing the release of the probiotic along the intestinal tract. There is also a need for a protective mixture that contains only approved ingredients generally regarded as safe (GRAS), and is less costly than those presently being used.

The present invention, in at least some embodiments, overcomes these drawbacks of the background art and provides a solution to these needs, by providing a composition and process for producing a composition for probiotic bacteria that are stable during processing, and for long periods of time at ambient temperatures and varying degrees of humidity.

In at least some embodiments, the present invention provides a fast and cost effective preparation process and protection in food products (foodstuffs). As described herein, the terms "food" and "foodstuffs" may be understood to encompass any type of nutritional product that is suitable for mammals, including but not limited to humans.

The present invention, in at least some embodiments, provides a composition comprising probiotic bacteria that is heat, oxygen and humidity resistant and that is suitable for a food product, wherein the composition is in the form of particles, the composition comprising: (a) a core composition containing the probiotic bacteria and a stabilizer, wherein the total amount of probiotics in the mixture is from about 10% to about 90% by weight of the core composition; (b) an innermost coating layer, layered on said core composition, comprising at least one hydrophobic solid fat or fatty acid having a melting point lower than 60° C.; (c) an intermediate coating layer layered on said innermost coating layer, which when present in an aqueous solution in the amount of 0.1% weight/weight over the weight of the solution, has a surface tension lower than 60 mN/m, when measured at 25° C.; and (d) an outer coating layer, layered on said intermediate coating layer.

The stabilizer may optionally comprise any type of oxygen scavenger, including but not limited to those containing L-cysteine base or hydrochloride, of which other examples are listed herein.

The core composition may also optionally comprise at least one sugar compound including but not limited to maltodextrin, trehalose, lactose, galactose, sucrose, fructose and the like, of which other examples are provided herein. Disaccharides, such as sucrose and trehalose, are attractive as protective agents within the core because they are actually help plants and microbial cells to remain in a state of suspended animation during periods of drought. Trehalose has been shown to be an effective protectant for a variety of biological materials, both in ambient air-drying and freeze-drying.

The core composition may also optionally comprise one or more other food grade ingredients, including but not limited to a filler, a surfactant and binder, of which various non-limiting examples are provided herein.

The innermost coating layer may optionally comprise at least one hydrophobic solid fat or fatty acid having a melting point lower than 50° C. and preferably higher than 25° C. The melting point is optionally preferably lower than 45° C. and higher than 30° C., and is optionally and most preferably lower than 40° C. and higher than 35° C. The innermost coating layer may optionally form a stable hydrophobic matrix which embeds the core composition within and/or forms a film around the probiotic core composition.

The intermediate coating layer, which when present in an aqueous solution in the amount of 0.1% weight/weight over the weight of the solution, optionally has a surface tension lower than 50 mN/m and preferably lower than 45 mN/m when measured at 25° C.

The outer coating layer optionally comprises a polymer having an oxygen transmission rate of less than 1000 cc/m$^2$/24 hr, preferably less than 500 cc/m$^2$/24 hr and most preferably less than 100 cc/m$^2$/24 hr measured at standard test conditions (which may for example be 73° F. (23° C.) and 0% RH). The polymer also optionally has a water vapor transmission rate of less than 400 g/m$^2$/day, preferably less than 350 g/m$^2$/day and most preferably less than 300 g/m$^2$/day.

The composition may optionally further comprise an additional humidity barrier coating layer, layered on the outer coating layer, for preventing further humidity penetration. The composition may optionally further comprise an enteric polymer, layered on the humidity barrier coating layer, which may further provide protection against such destructive characteristics of the gastrointestinal tract as low pH values and proteolytic enzymes.

The resultant composition is in a solid form which may optionally be any solid particulate form as described herein, including but not limited to granules, powder and the like. The stabilized composition is suitable for admixing/adding to food products including but not limited to chocolate, cheese, creams, sauces, mayonnaise and biscuit fill-in. The stabilized probiotic bacteria within the protective composition maintain their viability during manufacturing or preparation processes that involve exposure to high temperature, humidity and oxygen. The stabilized bacteria maintain their viability during storage conditions at ambient temperatures, in a humid oxygenated environment, even after they are added to a food product. An example of high temperature to be resisted is a tempering step during preparation of chocolate, or mixing within cream compositions.

The present invention, in at least some embodiments, relates to a process for the preparation of a food product containing the stabilized composition, in which the preparation process may optionally comprise a heating step, the product containing active probiotic bacteria, the method comprising i) preparing stabilized probiotic composition particles as described herein; ii) admixing said stabilized probiotic particles into a semi-final product; iii) heating the mixture of said probiotic particles and semi-final product at a predetermined temperature and for a predetermined time period; and vi) completion of said semi-final product containing said stabilized probiotic particles by cooling down said mixture, thereby obtaining said final product containing stabilized active probiotic bacteria showing high stability during the storage and shelf life of the final product. The term "semi-final product" describes a stage in the preparation of a food product as is known in the art, in which said food product does not yet contain all the components or has not yet passed all the preparation steps, and hence is not yet ready for the consumption.

The present invention, in at least some embodiments, provides stabilized probiotic particles for admixing to a food product, resistant to ambient temperature, humidity and oxygen, which can be prepared according to a variety of processes, including but not limited to hot melt processes, wet granulation or dry granulation. If the initial particle size of probiotics and other excipients included in the core composition is sufficient to enable the coating of the first coating layer, no granulation process is required.

A food product according to various embodiments of the present invention may be a product optionally having the form of a suspension, emulsion, or paste, as non-limiting examples. Non-limiting examples of such food products according to various embodiments of the present invention include but are not limited to creams, biscuits creams, biscuit fill-in, chocolates, sauces, cheese, mayonnaise and etc, in which the product is a health food product comprising probiotic bacteria which are stabilized as described above for long term storage and shelf life.

The present invention, in at least some embodiments, relates to healthy food beneficially affecting the consumer's intestinal microbial balance, wherein said heat-resistance and heat-processability are ensured by coating probiotic cores by layers which limit the transmission of heat, oxygen and humidity to the probiotic bacteria and so increase their resistance during preparation process and storage and thus extend the shelf life. By "consumer" it is meant any mammal consuming the product, including but not limited to humans.

BRIEF DESCRIPTION OF THE DRAWINGS

The above and other characteristics and advantages of the invention will be more readily apparent through the following examples, and with reference to the appended drawing, wherein.

DETAILED DESCRIPTION OF PREFERRED EMBODIMENTS

It has now been found that probiotic bacteria may be surprisingly efficiently stabilized for use in a food preparation process by a unique combination of coating layers having unique arrangement order. The bacteria were formulated in a core coated with coating layers, thereby obtaining probiotic compositions providing viable probiotic organisms even after a prolonged time of storage at ambient temperature at high humidity, the composition being further stable on storage and shelf life of the food stuff containing the protected probiotics according to the present invention and capable of administering viable bacteria to the gastrointestinal tracts after the oral administration.

The present invention, in at least some embodiments, provides a probiotic composition in particulate form to be used as healthy food additives. The present invention is particularly directed to a process for the preparation of protected probiotics against oxygen and humidity (water vapor) for incorporating into foodstuffs such as creams, biscuits creams, biscuit fill-in, chocolates, sauces, cheese, mayonnaise and etc.

In a preferred embodiment of the invention, said probiotic bacteria comprise at least one *Bifidobacterium animalis lactis*. The stabilized probiotic core granule or core mixing according to the invention is a coated granule, comprising at least three layered phases, for example a core and three coats, or a core and three or more coats. Usually, one of the coats is hydrophobic solid fat contributing mainly to prevention of water or humidity penetration into the core during the coating of the outer layer or during later stages. At least one other coat is an outer coating which is responsible for preventing transmission of humidity and oxygen into the core during the storage and shelf life, while the intermediate coating layer is present between these two coating layers and is responsible for providing binding and adhesion of the previous coats to each other wherein said intermediate coat may further provide oxygen and/or humidity resistance to the core. Such an intermediate coating may also optionally comprise a layer that contributes significantly to oxygen resistance, and also optionally provides a barrier against water or humidity penetration into the core; however, the stabilized probiotic granule of the invention may comprise more layers that contribute to the stability process of the bacteria, as well as to their stability during storing said food and during safe delivery of the bacteria to the intestines.

Figure 1:
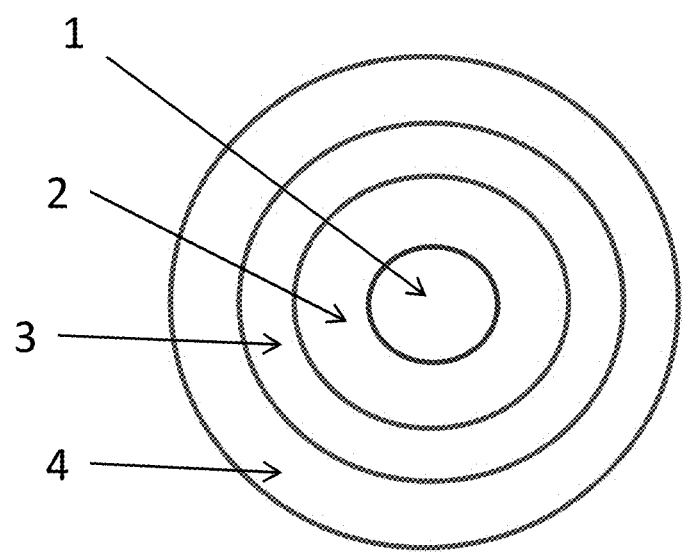
FIG. 1. shows a schematic diagram of a multiple-layered capsule according to one embodiment of the invention.

Schematic Description of the Composition According to at Least Some Embodiments of the Present Invention FIG. 1 shows a schematic diagram of a multiple-layered capsule according to a non-limiting, illustrative embodiment of the invention, to be provided (for example) through food; the encapsulation is designed to provide probiotic bacteria with maximum stability during storage and shelf life at ambient temperature by providing protection against oxygen and humidity during manufacturing process or preparation process as well as storage. As shown, the numbered labels indicate the components of the composition. Label "1" indicates the core, which comprises probiotic bacteria and a substrate such as stabilizer and optionally also a sugar and one or more other ingredients as indicated herein. Label "2" indicates the first layer adjacent to the core, which is the inner first sealing layer comprising a hydrophobic material, such as a solid fat for example. Label "3" indicates the intermediate layer adjacent to said inner layer, binding the outer layer to the inner layer. Label "4" indicates the outer layer adjacent to said intermediate layer, providing protection against oxygen and humidity (water vapor), and thus also supporting longer storage stability and shelf life at ambient temperature.

Figure 2:
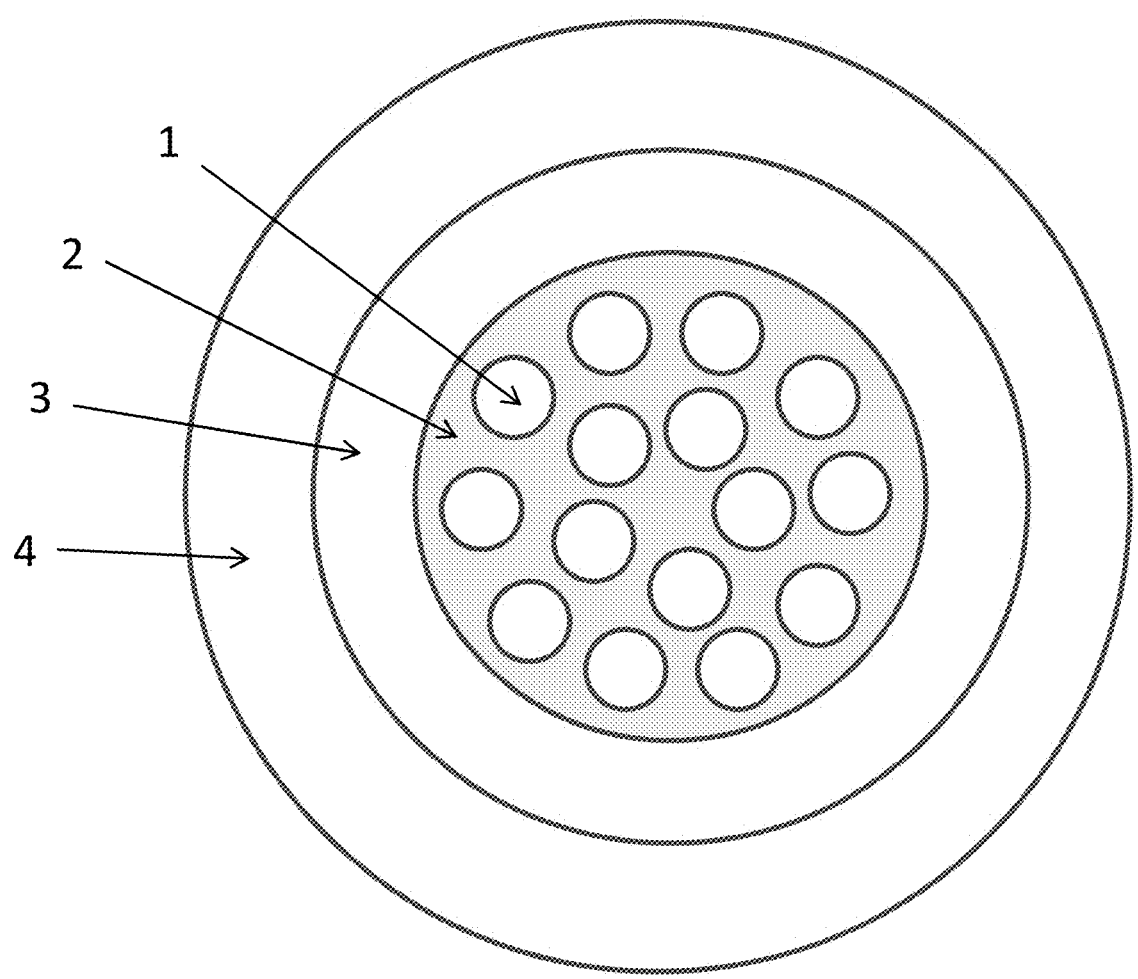
FIG. 2 shows a schematic diagram of a multiple-layered capsule according to one embodiment of the invention.

FIG. 2 shows a schematic diagram of a multiple-layered capsule according to another embodiment of the invention. As shown, the numbered labels indicate the components of the composition. Label "1" indicates multiple cores featuring probiotic bacteria and other possible excipients which may be included in the cores as described herein. Label "2" indicates a first fat coating layer, which is the innermost coating layer comprising at least one hydrophobic solid fat or fatty acid having a melting point lower than 60° C. and preferably higher than 25° C., forming a stable hydrophobic matrix which in which the probiotic cores are embedded. Label "3" indicates an intermediate layer, for which the aqueous solution of 0.1% has a surface tension lower than 60 mN/m. Label "4" indicates an outer layer, comprising a polymer having an oxygen transmission rate of less than 1000 cc/m2/24 hr.

Figure 3:
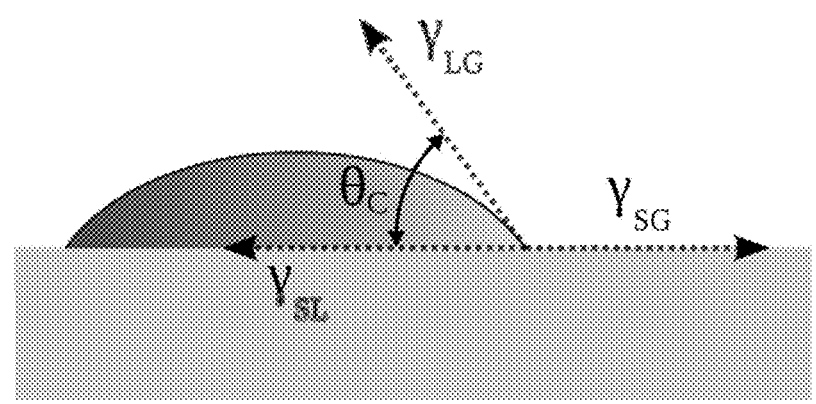
FIG. 3 shows a schematic diagram of a contact angle (θ) which is formed when a liquid does not completely spread on a substrate (usually a solid).

FIG. 3 shows a schematic diagram of a contact angle (θ) which is formed when a liquid does not completely spread on a substrate (usually a solid). It is a direct measure of interactions taking place between the participating phases. The contact angle is determined by drawing a tangent at the contact where the liquid and solid intersect. Contact angle is geometrically defined as the angle on the liquid side of the tangential line drawn through the three phase boundary where a liquid, gas and solid intersect, or two immiscible liquids and solid intersect.

Probiotics-Containing Particles

According to a preferred embodiment of the invention, the probiotic bacteria in said inner core are mixed with a stabilizer, optionally and preferably with at least one sugar and/or at least one oligosaccharide or polysaccharides (as a supplemental agent for the bacteria), and optionally other food grade additives such as fillers, binders, surfactant, and so forth.

Examples of probiotic bacteria include but are not limited to *Bacillus coagulans* GBI-30, 6086, *Bacillus subtilis* var natt, *Bifidobacterium* LAFTI® B94, *Bifidobacterium* sp LAFTI B94, *Bifidobacterium bifidum*, *Bifidobacterium bifidum* rosell-71, *Bifidobacterium breve*, *Bifidobacterium breve* Rosell-70, *Bifidobacterium infantis*, *Bifidobacterium lactis*, *Bifidobacterium longum*, *Bifidobacterium longum* Rosell-175, *Bifidobacterium animalis*, *Bifidobacterium animalis* subsp. *lactis* BB-12, *Bifidobacterium animalis* subsp. *lactis* HN019, *Bifidobacterium infantis* 35624, *Escherichia coli* M-17, *Escherichia coli* Nissle 1917, *Lactobacillus acidophilus*, *Lactobacillus acidophilus* LAFTI® L10, *Lactobacillus acidophilus* LAFTI L10, *Lactobacillus casei* LAFTI® L26, *Lactobacillus casei* LAFTI L26, *Lactobacillus brevis*, *Lactobacillus bulgaricus*, *Lactobacillus casei*, *Lactobacillus gasseri*, *Lactobacillus paracasei*, *Lactobacillus plantarum*, *Lactobacillus reuteri* ATTC 55730 (*Lactobacillus reuteri* SD2112), *Lactobacillus rhamnosus*, *Lactobacillus salivarius*, *Lactobacillus delbrueckii*, *Lactobacillus fermentum*, *Lactococcus lactis*, *Lactococcus lactis* subsp, *Lactococcus lactis* Rosell-1058, *Lactobacillus paracasei* St11 (or NCC2461) *Lactobacillus fortis* Nestlé, *Lactobacillus johnsonii* La1 (=*Lactobacillus* LC1, *Lactobacillus johnsonii* NCC533) Nestlé, *Lactobacillus rhamnosus* Rosell-11, *Lactobacillus acidophilus* Rosell-52, *Streptococcus thermophilus*, *Diacetylactis*, *Saccharomyces cerevisiae*, and a mixture thereof.

Sugar:

According to a preferred embodiment of the invention, the probiotic bacteria in the core composition are mixed with a sugar. The sugar preferably comprises at least one material that is also a supplemental agent for the probiotic bacteria. It should be noted that optionally the sugar is the supplemental agent itself. A supplemental agent as used herein refers to an agent with a nutritional and/or protective role, for example.

The sugar may optionally comprise any one or more of the following: monosaccharides such as trioses including ketotriose (dihydroxyacetone) and aldotriose (glyceraldehyde), tetroses such as ketotetrose (erythrulose), aldotetroses (erythrose, threose) and ketopentose (ribulose, xylulose), pentoses such as aldopentose (ribose, arabinose, xylose, lyxose), deoxy sugar (deoxyribose) and ketohexose (psicose, fructose, sorbose, tagatose), hexoses such as aldohexose (allose, altrose, glucose, mannose, gulose, idose, galactose, talose), deoxy sugar (fucose, fuculose, rhamnose)

and heptose such as (sedoheptulose), and octose and nonose (neuraminic acid). The substrate may comprise multiple saccharides such as 1) disaccharides, such as sucrose, lactose, maltose, trehalose, turanose, and cellobiose, 2) trisaccharides such as raffinose, melezitose and maltotriose, 3) tetrasaccharides such as acarbose and stachyose, 4) other oligosaccharides such as fructooligosaccharide (FOS), galactooligosaccharides (GOS) and mannan-oligosaccharides (MOS), 5) polysaccharides such as glucose-based polysaccharides/glucan including glycogen starch (amylose, amylopectin), cellulose, dextrin, dextran, beta-glucan (zymosan, lentinan, sizofiran), and maltodextrin, fructose-based polysaccharides/fructan including inulin, levan beta 2-6, mannose-based polysaccharides (mannan), galactose-based polysaccharides (galactan), and N-acetylglucosamine-based polysaccharides including chitin. Other polysaccharides may be included, including but not limited to gums such as arabic gum (gum acacia).

Stabilizer and Antioxidant (Oxygen Scavenger):

According to a preferred embodiment of the invention, the probiotic bacteria in said inner core are mixed with a stabilizer which may be selected from the group consisting of dipotassium edetate, disodium edetate, edetate calcium disodium, edetic acid, fumaric acid, malic acid, maltol, sodium edetate, trisodium edetate. According to preferred embodiments of the present invention, the core further comprises an antioxidant. Preferably, the antioxidant is selected from the group consisting of L-cysteine hydrochloride, L-cysteine base, 4,4 (2,3 dimethyl tetramethylene dipyrocatechol), tocopherol-rich extract (natural vitamin E), α-tocopherol (synthetic Vitamin E), β-tocopherol, γ-tocopherol, δ-tocopherol, butylhydroxinon, butyl hydroxyanisole (BHA), butyl hydroxytoluene (BHT), propyl gallate, octyl gallate, dodecyl gallate, tertiary butylhydroquinone (TBHQ), fumaric acid, malic acid, ascorbic acid (Vitamin C), sodium ascorbate, calcium ascorbate, potassium ascorbate, ascorbyl palmitate, and ascorbyl stearate. According to some embodiments of the present invention, the core further comprises both a stabilizer and an antioxidant. Without wishing to be limited by a single hypothesis or theory, stabilizing agents and antioxidants may optionally be differentiated. According to one preferred embodiment, the antioxidant is L-cysteine hydrochloride or L-cysteine base.

Filler and Binder:

According to some embodiments of the present invention, the core further comprises both filler and binder. Examples of fillers include but are not limited to, for example, microcrystalline cellulose, a sugar, such as lactose, glucose, galactose, fructose, or sucrose; dicalcium phosphate; sugar alcohols such as sorbitol, manitol, mantitol, lactitol, xylitol, isomalt, erythritol, and hydrogenated starch hydrolysates; corn starch; and potato starch; and/or a mixture thereof. More preferably, the filler is lactose. Examples of binders include Povidone (PVP: polyvinyl pyrrolidone), Copovidone (copolymer of vinyl pyrrolidone and vinyl acetate), polyvinyl alcohol, low molecular weight HPC (hydroxypropyl cellulose), low molecular weight HPMC (hydroxypropyl methylcellulose), low molecular weight hydroxymethyl cellulose (MC), low molecular weight sodium carboxy methyl cellulose, low molecular weight hydroxyethylcellulose, low molecular weight hydroxymethylcellulose, cellulose acetate, gelatin, hydrolyzed gelatin, polyethylene oxide, acacia, dextrin, starch, and water soluble polyacrylates and polymethacrylates, low molecular weight ethylcellulose or a mixture thereof. More preferably, the binder is low molecular weight HPMC. When using a hot melt for making granulation one or more of the following, having a melting point below 60° C., can be used as a binder: a solid fat, fatty acid, a wax or a polyethylene glycol (PEG). For this purpose first the binder is melted and then sprayed onto the dry mixture of powders which is at a temperature which is well below the melting point of the binder.

Surfactant:

According to some embodiments of the present invention, the core further comprises a probiotics friendly surfactant such as nonionic surfactants. Examples of nonionic surfactant include but are not limited to, for example, tween 80 (polysorbate 80, Polyoxyethylene (20) sorbitan monooleate), tween 20 (polysorbate 20, Polyoxyethylene (20) sorbitan monolaurate), Tween 85 (Polyoxyethylene sorbitan trioleate), glycereth-2-cocoate (Levenol® C-421), glycereth-6-cocoate (Levenol® F-200), glycereth-7-cocoate (Levenol® C-301), glycereth-17-cocoate (Levenol® C-201) or a mixture thereof.

First Coating Layer:

According to a preferred embodiment of the invention particles of said core mixture are coated with an inner coating layer comprising a hydrophobic solid fat or fatty acid or a wax having a melting point below 50° C., forming a stable hydrophobic film or matrix which embeds the probiotic, preventing or reducing the penetration of water or humidity into said core during the further coating processes. As used herein the term fats consist of a wide group of hydrophobic compounds that are generally soluble in organic solvents and largely insoluble in water. Chemically, fats are generally triesters of glycerol and fatty acids. Fats may be either solid or liquid at room temperature, depending on their structure and composition. Although the words "oils", "fats", and "lipids" are all used to refer to fats, "oils" is usually used to refer to fats that are liquids at normal room temperature, while "fats" is usually used to refer to fats that are solids at normal room temperature. "Lipids" is used to refer to both liquid and solid fats, along with other related substances. The word "oil" is used for any substance that does not mix with water and has a greasy feel, such as petroleum (or crude oil) and heating oil, regardless of its chemical structure. Examples of fats according to the present invention include but are not limited to Fats as described above, fatty acids, fatty acid esters, fatty acid triesters, slats of fatty acids such as aluminum, sodium, potassium and magnesium, fatty alcohols, phospholipids, solid lipids, waxes, and a combination thereof having a melting point lower than 50° C. and higher than 25° C., preferably lower than 45° C. and higher than 30° C. and most preferably lower than 40° C. and higher than 35° C. forming a stable hydrophobic film or matrix which embeds the probiotic or forms film around the probiotics core particles. The solid fat is optionally and preferably at least one of lauric acid, hydrogenated coconut oil, cacao butter and a combination thereof.

According to another preferred embodiment of the invention particles of said core mixture are granulated by said hydrophobic solid fat or fatty acid using a hot melt granulation process. In this case a melt of said hydrophobic solid fat or fatty acid is used for granulation of said core particles therefore, said hydrophobic solid fat or fatty acid constitutes a matrix in which said core particles are embedded thus said hydrophobic solid fat or fatty acid functions as both binder for granulation and first coating layer of said core particles. In other words said hot melt of said hydrophobic solid fat or fatty acid may simultaneously constitute, by hot melt granulation process, both core binder as well as the first inner coating layer.

Intermediate Coating Layer:

According to a preferred embodiment of the invention, particles of said core mixture coated with said inner coating layer are coated with an intermediate coating layer whose the aqueous solution of 0.1% has a surface tension lower than 60 mN/m, preferably lower than 50 mN/m and most preferably lower than 45 mN/m measured at 25° C. for adjusting surface tension for further coating with outer coating layer.

Surface tension (ST) is a property of the surface of a liquid that allows it to resist an external force. In the other word surface tension is the measurement of the cohesive (excess) energy present at a gas/liquid interface. The molecules of a liquid attract each other. The interactions of a molecule in the bulk of a liquid are balanced by an equally attractive force in all directions. Molecules on the surface of a liquid experience an imbalance of forces as indicated below. The net effect of this situation is the presence of free energy at the surface. The excess energy is called surface free energy and can be quantified as a measurement of energy/area. It is also possible to describe this situation as having a line tension or surface tension, which is quantified as a force/length measurement. The common units for surface tension are dynes/cm or mN/m. These units are equivalent.

Polar liquids, such as water, have strong intermolecular interactions and thus high surface tensions. Any factor which decreases the strength of this interaction will lower surface tension. Thus an increase in the temperature of this system will lower surface tension. Any contamination, especially by surfactants, will lower surface tension and lower surface free energy. Some surface tension values of common liquids and solvents are shown in the following table, Table 1.

TABLE 1 surface tension values

| Substance | $\gamma$ (mN/m) | $\gamma^p$ (mN/m) | $\gamma^d$ (mN/m) |
|---|---|---|---|
| Water | 72.8 | 51.0 | 21.8 |
| Glycerol | 64 | 30 | 34 |
| Ethylene glycol | 48 | 19 | 29 |
| Dimethyl sulfoxide | 44 | 8 | 36 |
| Benzyl alcohol | 39 | 11.4 | 28.6 |
| Toluene | 28.4 | 2.3 | 26.10 |
| Hexane | 18.4 | — | 18.4 |
| Acetone | 23.7 | — | 23.7 |
| Chloroform | 27.15 | — | 27.15 |
| Diiodomethane | 50.8 | — | 50.8 |

The adhesion and uniformity of a film are also influenced by the forces which act between the coating formulation which is in a solution form and the core surface of the film coated surface. Therefore, coating formulations for certain core surface can be optimized via determination of wetting behavior, the measure of which is the contact or wetting angle. This is the angle that forms between a liquid droplet and the surface of the solid body to which it is applied.

When a liquid does not completely spread on a substrate (usually a solid) a contact angle ($\theta$) is formed which is geometrically defined as the angle on the liquid side of the tangential line drawn through the three phase boundary where a liquid, gas and solid intersect, or two immiscible liquids and solid intersect.

It is a direct measure of interactions taking place between the participating phases. The contact angle is determined by drawing a tangent at the contact where the liquid and solid intersect.

The contact angle is small when the core surface is evenly wetted by spreading droplets. If the liquid droplet forms a defined angle, the size of the contact angle is described by the Young-Dupre equation;

$$\gamma_{SG} - \gamma_{SL} = \gamma_{LG} \cdot \cos\theta$$

$\theta$=Contact angle
$\gamma_{SG}$=surface tension of the solid body
$\gamma_{LG}$=surface tension of the liquid
$\gamma_{SL}$=interfacial tension between liquid and solid body (cannot be measured directly)

With the aid of this equation it is possible to estimate the surface tension of a solid body by measuring the relevant contact angles. If one measured them with liquid of varying surface tension and plots their cosines as a function of the surface tension of the liquids, the result is a straight line. The abscissa value of the intersection of the straight line with cos $\theta$=1 is referred to as the critical surface tension of wetting $\gamma_C$. A liquid with a surface tension smaller than $\gamma_C$, wets the solid in question.

The wetting or contact angle can be measured with ease by means of telescopic goniometers (e.g. LuW Wettability Tester by AB Lorentzenu. Wettre, S-10028 Stockholm 49). In many cases, the quantity $\gamma_C$ does not suffice to characterize polymer surfaces since it depends amongst other factors on the polar character of the test liquids. This method can, however, be improved by dividing $\gamma$ into non polar part $\gamma^d$ (caused by dispersion forces) and a polar part $\gamma^p$ (caused by dipolar interactions and hydrogen bonds).

$$\gamma_L = \gamma_L^p + \gamma_L^d$$

$$\gamma_S = \gamma_S^p + \gamma_S^d$$

$\gamma_L$=surface tension of the test liquid
$\gamma_S$=surface tension of the solid body
$\gamma_S^p$ and $\gamma_S^d$ can be determined by means of the following equation:

$$1+(\cos\theta/2)(\gamma_L/\sqrt{\gamma_L^d}) = \sqrt{\gamma_S^d} + \sqrt{\gamma_S^p} \cdot \sqrt{(\gamma_L - \gamma_L^d)/\gamma_L^d}$$

If $1+(\cos\theta/2)(\gamma_L/\sqrt{\gamma_L^d})$ is plotted against $\sqrt{(\gamma_L - \gamma_L^d)/\gamma_L^d}$, straight lines are obtained, from the slops and ordinate intercepts of which $\gamma_S^p$ and $\gamma_S^d$ can be determined thus $\gamma S$ calculated.

$\gamma_C$ and $\gamma_S$ are approximately, but not exactly, the same. Since the measurement is also influenced by irregularities of the polymer surfaces, one cannot obtain the ture contact angle $\theta$ but rather the quantity $\theta'$. Both quantities are linked by the relationship;

Roughness factor $r = \cos\theta'/\cos\theta$

The lower the surface tension of the coating formulation against that of the core surface, the better the droplets will spread on the surface. If formulations with organic solvents are used, which wet the surface very well' the contact angle will be close to zero. The surface tensions of such formulations are then about 20 to 30 mN/m. Aqueous coating dispersion of some polymer like EUDRAGIT L 30 D type shows low surface tension in the range of 40 to 45 mN/m.

Contact angle measurements may optionally provide the following information, which may be useful for selecting coating materials according to at least some embodiments of the present invention (without wishing to be limited by a closed list):

1. Smaller contact angles give smoother film coatings
2. The contact angle becomes smaller with decreasing porosity and film former concentration.
3. Solvents with high boiling point and high dielectric constant reduce the contact angle.

4. The higher the critical surface tension of core, the better the adhesion of the film to the core.
5. The smaller the contact angle, the better the adhesion of the film to the core.

The critical surface tension of said core or granules coated with a hydrophobic solid fat is essentially very low. Therefore for providing better spreading and thus better adhesion of the outer coating layer film to the core, according to at least some embodiments it is desirable to reduce the surface free energy at the interface between the surface of the fat coated core/granules and the solution of the outer coating layer polymer.

According to a preferred embodiment of the present invention, particles of said core mixture coated with said hydrophobic solid fat (inner coating layer) are coated with an intermediate coating layer whose the aqueous solution of 0.1% has a surface tension lower than 60 mN/m, preferably lower than 50 mN/m and most preferably lower than 45 mN/m measured at 25° C. for reducing the surface free energy at the interface between the surface of the fat coated core/granules and the solution of the outer coating layer polymer.

The following table, Table 2, shows for example the surface tension of the solution of some water soluble polymers. The surface tension was measured at 25° C., 0.1% aqueous solution of the polymers.

TABLE 2 surface tension values of selected polymers

| Polymer | Surface Tension mN/m |
| --- | --- |
| Sodium Carboxymethylcellulose (Na-CMC) | 71.0 |
| Hydroxyethyl cellulose (HEC) | 66.8 |
| Hydroxypropyl cellulose (HPC) | 43.6 |
| Hydroxypropyl methyl cellulose (HPMC) | 46-51 |
| Hydroxymethyl cellulose (HMC) | 50-55 |

Non-limiting examples of polymers which may be used as intermediate coating layer include Hydroxypropylmethylcellulose (HPMC), Hydroxypropylethylcellulose (HPEC), Hydroxypropylcellulose (HPC), hydroxypropylethylcellulose (HPEC), hydroxymethylpropylcellulose (HMPC), ethylhydroxyethylcellulose (EHEC) (Ethulose), hydroxyethylmethylcellulose (NEMC), hydroxymethylethylcellulose (HMEC), propylhydroxyethylcellulose (PHEC), methylhydroxyethylcellulose (MHEC), hydrophobically modified hydroxyethylcellulose (NEXTON), carboxymethylhydroxyethylcellulose (CMHEC), Methylcellulose, Ethylcellulose, water soluble vinyl acetate copolymers, gums, polysaccharides such as alginic acid and alginates such as ammonia alginate, sodium alginate, potassium alginate, pH-sensitive polymers for example enteric polymers including phthalate derivatives such as acid phthalate of carbohydrates, amylose acetate phthalate, cellulose acetate phthalate (CAP), other cellulose ester phthalates, cellulose ether phthalates, hydroxypropylcellulose phthalate (NPCP), hydroxypropylethylcellulose phthalate (HPECP), hydroxyproplymethylcellulose phthalate (HPMCP), hydroxyproplymethylcellulose acetate succinate (HPMCAS), methylcellulose phthalate (MCP), polyvinyl acetate phthalate (PVAcP), polyvinyl acetate hydrogen phthalate, sodium CAP, starch acid phthalate, cellulose acetate trimellitate (CAT), styrene-maleic acid dibutyl phthalate copolymer, styrene-maleic acid/polyvinylacetate phthalate copolymer, styrene and maleic acid copolymers, polyacrylic acid derivatives such as acrylic acid and acrylic ester copolymers, polymethacrylic acid and esters thereof, polyacrylic and methacrylic acid copolymers, shellac, and vinyl acetate and crotonic acid copolymers. Preferred pH-sensitive polymers include shellac, phthalate derivatives, CAT, HPMCAS, polyacrylic acid derivatives, particularly copolymers comprising acrylic acid and at least one acrylic acid ester, Eudragit™ S (poly (methacrylic acid, methyl methacrylate)1:2); Eudragit L100™ (poly(methacrylic acid, methyl methacrylate)1:1); Eudragit L30D™, (poly(methacrylic acid, ethyl acrylate)1:1); and (Eudragit L100-55) (poly(methacrylic acid, ethyl acrylate)1:1) (Eudragit™ L is an anionic polymer synthesized from methacrylic acid and methacrylic acid methyl ester), polymethyl methacrylate blended with acrylic acid and acrylic ester copolymers, alginic acid and alginates such as ammonia alginate, sodium, potassium, magnesium or calcium alginate, vinyl acetate copolymers, polyvinyl acetate 30D (30% dispersion in water), a poly(dimethylaminoethylacrylate) which is a neutral methacrylic ester available from Rohm Pharma (Degusa) under the name "Eudragit E™, a copolymer of methylmethacrylate and ethylacrylate with small portion of trimethylammonioethyl methacrylate chloride (Eudragit RL, Eudragit RS), a copolymer of methylmethacrylate and ethylacrylate (Eudragit NE 30D), Zein, shellac, gums, polysaccharides and or the combination thereof.

Outer Layer

According to at least some embodiments of the present invention, the composition further comprises an outer coating layer comprising a polymer having oxygen transmission rate of less than 1000 cc/m$^2$/24 hr, preferably less than 500 cc/m$^2$/24 hr and most preferably less than 100 cc/m$^2$/24 hr measured at standard test conditions i.e. 73° F. (23° C.) and 0% RH, and a water vapor transmission rate of less than 400 g/m$^2$/day, preferably less than 350 g/m$^2$/day and most preferably less than 300 g/m$^2$/day coats said water sealed coated particles having an adjusted surface for reducing or preventing the transmission of oxygen and humidity into the core thereby obtaining a multiple-layered particle containing probiotics demonstrating improved stability against both humidity as well as oxygen. Various suitable examples of such polymers are described below.

Water Vapor Permeability (WVP) of Films

The water vapor permeability is one of the most important properties of said outer layer coating films mainly because of the importance of the role of water in deteriorative reactions.

Water acts as a solvent or carrier and causes texture degradation, chemical and enzymatic reactions, and thus is destructive of probiotics. Also the water activity of foods is an important parameter in relation with the shelf-life of the food and food-containing probiotics. In low-moisture foods and probiotics, low levels of water activity must be maintained to minimize the deteriorative chemical and enzymatic reactions and to prevent the texture degradation. The composition of film forming materials (hydrophilic and hydrophobic character), temperature and relative humidity of the environment affect the water vapor permeability of the films.

When considering a suitable barrier in foods-containing probiotics the barrier properties of the films are important parameters.

Polysaccharide films and coatings are generally good barriers against oxygen and carbon dioxide and have good mechanical properties but their barrier property against water vapor is poor because of the their hydrophilic character.

To add an extra hydrophobic component e.g. a lipid (waxes, fatty acids) in the film and produce a composite film is one way to achieve a better water vapor barrier. Here the lipid component serves as the barrier against water vapor. By adding lipid, the hydrophobicity of the film is increased and as a result of this case water vapor barrier property of the film increases.

Water Vapor Permeability of a film is a constant that should be independent of the driving force on the water vapor transmission. When a film is under different water vapor pressure gradients (at the same temperature), the flow of water vapor through the film differs, but their calculated permeability should be the same. This behavior does not happen with hydrophilic films where water molecules interact with polar groups in the film structure causing plasticization or swelling.

Another assumption inherent to the calculation of permeability is its independence from film thickness. This assumption is not true for hydrophilic films. Because of that experimentally determined water vapor permeability of most films applied only to the specific water vapor gradients used during the testing and for the specific thickness of the tested specimens, it has been proposed the use of the terms "Effective Permeability" or "Apparent Permeability."

Moisture transport mechanism through a composite depends upon the material and environmental conditions. Permeability has two different features in case of composites. First; in non-porous membranes, permeation can occur by solution and diffusion; and the other; simultaneous permeation through open pores is possible in porous membrane.

There are various methods of measuring permeability. Weight loss measurements are of importance to determine permeability characteristics. Water vapor permeability is usually determined by direct weighing because, despite its inherent problems, mainly related to water properties such as high solubility and cluster formation within the polymer and tendency to plasticize the polymer matrix, it is simple and relatively reliable method. The major disadvantage of this method resides in its weakness to provide information for a kinetic profile, when such a response is required.

Another measurement method is based on the standard described in ASTM E96-80 (standard test method procedure for water vapor permeability). According to this method water vapor permeability is determined gravimetrically and generally, the applied procedures are nearly the same in many research papers that are related with this purpose. In this procedure firstly, the test film is sealed to a glass permeation cell which contain anhydrous calcium chloride (CaCl2), or silica gel (Relative vapor pressure; RVP=0) and then the cell is placed in the desiccators maintained at specific relative humidity and temperature (generally 300 C, 22% RH) with magnesium nitrate or potassium acetate. Permeation cells are continuously weighed and recorded, and the water vapor that transferred through the film and absorbed by the desiccant are determined by measuring the weight gain. Changes in weight of the cell were plotted as a function of time. When the relationship between weight gain ($\Delta w$) and time ($\Delta t$) is linear, the slope of the plot is used to calculate the water vapor transmission rate (WVTR) and water vapor permeability (WVP). Slope is calculated by linear regression and correlation coefficient ($r2>>0.99$).

The WVTR is calculated from the slope ($\Delta w/\Delta t$) of the straight line divided by the test area (A), (g s−1 m−2);

$$WVTR=\Delta w/(\Delta t \cdot A)(g \cdot m-2 \cdot s-1)$$

where $\Delta w/\Delta t$=transfer rate, amount of moisture loss per unit of time (g·s−1);
A=area exposed to moisture transfer (m2)
The WVP (kg Pa−1 s−1 m−1) is calculated as;

$$WVP=[WVTR/S(R1-R2)] \cdot d$$

where S=saturation vapor pressure (Pa) of water at test temperature, R1=RVP (relative vapor pressure) in the desiccator, R2=RVP in the permeation cell, and d=film thickness (m). At least three replicates of each film should be tested for WVP and all films should be equilibrated with specific RH before permeability determination.

The water vapor permeability can also be calculated from the WVTR as follows;

$$P=WVTR \cdot L/\Delta p (g/m^2 \cdot s \cdot Pa)$$

L=film thickness (m); $\Delta p$=water vapor pressure gradient between the two sides of the film (Pa); P=film permeability (g·m−2·s−1Pa−1).

The rate of permeation is generally expressed by the permeability (P) rather than by a diffusion coefficient (D) and the solubility (S) of the penetrant in the film. When there is no interaction between the water vapor and film, these laws can apply for homogeneous materials. Then, permeability follows a solution—diffusion model as;

$$P=D \cdot S$$

where D is the diffusion coefficient and the S is the slope of the sorption isotherm and is constant for the linear sorption isotherm. The diffusion coefficient describes the movement of permeant molecule through a polymer, and thus represents a kinetic property of the polymer-permeant system.

As a result of the hydrophilic characteristics of polysaccharide films, the water vapor permeability of films is related to their thickness. The permeability values increase with the increasing thickness of the films.

Thickness of films and the molecular weight (MW) of the film forming polymers may also affect both water vapor permeability (WVP) and oxygen permeability (OP) of the films.

Oxygen Transmission Determination (OTR)

Oxygen transmission rate is the steady state rate at which oxygen gas permeates through a film at specified conditions of temperature and relative humidity. Values are expressed in cc/100 in2/24 hr in US standard units and cc/m2/24 hr in metric (or SI) units.

To assess the protective function which the coating performs on the core, its gas permeability is measured. According to at least some embodiments of the present invention, the most critical gas for improved stability of the probiotic bacteria is oxygen. It is well known that probiotic bacteria are anaerobic microorganism where their vitality may significantly be reduced upon exposing to oxygen. Therefore for providing long term stability and receiving an extended shelf life for probiotic bacteria the outer layer preferably provides a significant oxygen barrier.

The gas permeability, q, (ml/m^2·day·atm) (DIN 53380) is defined as the volume of a gas converted to 0° C. and 760 torr which permeates 1 m^2 of the film to be tested within one day at a specific temperature and pressure gradient. It is therefore calculated according to the following formula;

$$q=\{T_o \cdot P_u/[P_o \cdot T \cdot A(P_b-P_u)]\} \cdot 24 \cdot Q \cdot (\Delta x/\Delta t) \cdot 10^4$$

$P_o$=normal pressure in atm
$T_o$=normal temperature in K
T=experimental temperature in K
A=sample area in m^2
T=time interval in hrs between two measurements
$P_b$=atmospheric pressure in atm
$P_u$=pressure in test chamber between sample and mercury thread
Q=cross section of capillaries in cm
$\Delta x/\Delta t$=sink rate of the mercury thread in cm/hr The following table, Table 3, shows OTR and WVTR of some water soluble polymers for example.

TABLE 3

OTR and WVTR values

| Film Forming Polymer | Oxygen Transmission rate, Cm^3/m2/atm O2 day | Water vapor Transmission rate, g/m2/day |
|---|---|---|
| HPC, Klucel EF | Medium 776 | Low 126 |
| CMC, Aqualon or Blanose 7L | Low 18 | Low 228 |
| HEC, Natrosol 250L | Low 33 | Medium 360 |
| HPMC 5cps | High 3180 | High 420 |

Non-limiting examples of suitable outer layer coating polymer include water-soluble, hydrophilic polymers, such as, for example, polyvinyl alcohol (PVA), Povidone (PVP: polyvinyl pyrrolidone), Copovidone (copolymer of vinyl pyrrolidone and vinyl acetate), Kollicoat Protect (BASF) which is a mixture of Kollicoat IR (a polyvinyl alcohol (PVA)-polyethylene glycol (PEG) graft copolymer) and polyvinyl alcohol (PVA), Opadry AMB (Colorcon) which is a mixture based on PVA, Aquarius MG which is a cellulosic-based polymer containing natural wax, lecithin, xanthan gum and talc, low molecular weight HPC (hydroxypropyl cellulose), low molecular weight HEC (hydroxyethyl cellulose), low molecular weight carboxy methyl cellulose such as 7LF or 7L2P, or a mixture thereof. In some cases mixture of water soluble polymers with insoluble agents such as waxes, fats, fattu acids, and etc. may be of benefit.

More preferably the outer coating polymers are carboxy methyl cellulose such as 7LF or 7L2P, low molecular weight of hydroxyethyl cellulose (HEC) and low molecular weight HPC (hydroxypropyl cellulose)

Exterior Coating Layer

According to at least some embodiments of the present invention, the composition comprises an exterior coating layer comprising a polymer having a water vapor transmission rate of less than 400 g/m²/day, preferably less than 300 g/m²/day and most preferably less than 200 g/m²/day, which coats said oxygen and humidity sealed coated particles for further reducing or preventing the transmission of humidity into the core thereby obtaining a multiple-layered particle containing probiotics demonstrating improved stability against humidity as well.

Non-limiting examples of polymers that are suitable for the exterior coating layer include water-soluble, hydrophilic polymers, such as, for example, polyvinyl alcohol (PVA), Povidone (PVP: polyvinyl pyrrolidone), Copovidone (copolymer of vinyl pyrrolidone and vinyl acetate), Kollicoat Protect (BASF) which is a mixture of Kollicoat IR (a polyvinyl alcohol (PVA)-polyethylene glycol (PEG) graft copolymer) and polyvinyl alcohol (PVA), Opadry AMB (Colorcon) which is a mixture based on PVA, Aquarius MG which is a cellulosic-based polymer containing natural wax, lecithin, xanthan gum and talc, low molecular weight HPC (hydroxypropyl cellulose), low molecular weight carboxy methyl cellulose such as 7LF or 7L2P, or a mixture thereof. In some cases a mixture of water soluble polymers with insoluble agents such as waxes, fats, fatty acids, and so forth, may be of benefit.

More preferably the exterior coating polymers are polyvinyl alcohol, Kollicoat Protect (BASF) which is a mixture of Kollicoat IR (a polyvinyl alcohol (PVA)-polyethylene glycol (PEG) graft copolymer) and polyvinyl alcohol (PVA), Opadry AMB (Colorcon) which is a mixture based on PVA, low molecular weight HPC (hydroxypropyl cellulose) and Aquarius MG which is a cellulosic-based polymer containing natural wax. These polymers provide superior barrier properties against water vapor/humidity penetration into the core material.

Enteric Coating Layer

According to preferred embodiments of the present invention the core particles are further optionally coated by an enteric polymer which may further provide protection against destructive conditions present in the gastrointestinal tract for example.

Non-limiting examples of suitable enteric polymers include pH-sensitive polymers, acid phthalate of carbohydrates, amylose acetate phthalate, cellulose acetate phthalate (CAP), other cellulose ester phthalates, cellulose ether phthalates, hydroxypropylcellulose phthalate (NPCP), hydroxypropylethylcellulose phthalate (HPECP), hydroxyproplymethylcellulose phthalate (HPMCP), hydroxyproplymethylcellulose acetate succinate (HPMCAS), methylcellulose phthalate (MCP), polyvinyl acetate phthalate (PVAcP), polyvinyl acetate hydrogen phthalate, sodium CAP, starch acid phthalate, cellulose acetate trimellitate (CAT), styrene and maleic acid copolymers, styrene-maleic acid dibutyl phthalate copolymer, styrene-maleic acid/polyvinylacetate phthalate copolymer, polyacrylic acid derivatives such as acrylic acid and acrylic ester copolymers, polymethacrylic acid and esters thereof, polyacrylic and methacrylic acid copolymers, polyacrylic acid derivatives such as particularly copolymers comprising acrylic acid and at least one acrylic acid ester, Eudragit S™ (poly(methacrylic acid, methyl methacrylate)1:2); Eudragit L™ which is an anionic polymer synthesized from methacrylic acid and methacrylic acid methyl ester), Eudragit L100™ (poly (methacrylic acid, methyl methacrylate)1:1); Eudragit L30D™, (poly(methacrylic acid, ethyl acrylate)1:1); and Eudragit L100-55™ (poly(methacrylic acid, ethyl acrylate) 1:1), polymethyl methacrylate blended with acrylic acid and acrylic ester copolymers, alginic acid and alginates such as ammonia alginate, sodium, potassium, magnesium or calcium alginate.

Process for Preparation of a Stabilized Probiotic Composition According to at Least Some Embodiments of the Present Invention The present invention provides a process for the preparation of heat, oxygen and humidity resisting probiotic bacteria for a food product. In an embodiment of the invention, said stabilized probiotic particles are added to a food product such as such as creams, baked goods, biscuit creams or fill-in material, chocolates, sauces, cheese, mayonnaise and so forth.

In a preferred embodiment, the preferred process of the invention comprises preparation of a core composition in form of solid particulate matter containing probiotic bacteria, followed by layering of various coating layers on the particulate core composition. The core composition may optionally be prepared by any suitable method for preparing particulate matter, including but not limited to dry mix, wet granulation, dry granulation or hot melt (optionally in the form of a granulation process).

The core composition, prepared according to one of the above processes, contains at least the probiotic bacteria and a stabilizer, wherein the total amount of probiotics in the mixture is from about 10% to about 90% by weight of the core composition.

The stabilizer may optionally comprise any type of oxygen scavenger, including but not limited to those containing L-cysteine base or hydrochloride, of which other examples are listed herein.

The core composition may also optionally comprise at least one sugar compound including but not limited to maltodextrin, trehalose, lactose, galactose, sucrose, fructose and the like, of which other examples are provided herein. Disaccharides, such as sucrose and trehalose, are attractive as protective agents within the core because they are actually help plants and microbial cells to remain in a state of suspended animation during periods of drought. Trehalose has been shown to be an effective protectant for a variety of biological materials, both in ambient air-drying and freeze-drying.

The core composition may also optionally comprise one or more other food grade ingredients, including but not limited to a filler, a surfactant and binder, of which various non-limiting examples are provided herein.

These various ingredients may optionally be added sequentially during the core preparation process or alternatively may optionally be added together in any suitable combination.

Once the core composition has been formed, it is coated with an innermost coating layer, layered on said core composition, comprising at least one hydrophobic solid fat or fatty acid having a melting point lower than 60° C.

The innermost coating layer may optionally comprise at least one hydrophobic solid fat or fatty acid having a melting point lower than 50° C. and preferably higher than 25° C. The melting point is optionally preferably lower than 45° C. and higher than 30° C., and is optionally and most preferably lower than 40° C. and higher than 35° C. The innermost coating layer may optionally form a stable hydrophobic matrix which embeds the core composition within and/or forms a film around the probiotic core composition.

Next, the intermediate coating layer is layered over the innermost coating layer. As previously described with regard to the intermediate coating layer, when present in an aqueous solution in the amount of 0.1% weight/weight over the weight of the solution, the coating layer material has a surface tension lower than 60 mN/m, when measured at 25° C. The intermediate coating layer, which when present in an aqueous solution in the amount of 0.1% weight/weight over the weight of the solution, optionally has a surface tension lower than 50 mN/m and preferably lower than 45 mN/m when measured at 25° C. The intermediate coating layer optionally comprises at least one plasticizer selected from the group consisting of polyethylene glycol (PEG), triethyl citrate and triacetin.

Next an outer coating layer is layered over the intermediate coating layer. The outer coating layer optionally comprises a polymer having an oxygen transmission rate of less than 1000 cc/m$^2$/24 hr, preferably less than 500 cc/m$^2$/24 hr and most preferably less than 100 cc/m$^2$/24 hr measured at standard test conditions (which may for example be 73° F. (23° C.) and 0% RH). The polymer also optionally has a water vapor transmission rate of less than 400 g/m$^2$/day, preferably less than 350 g/m$^2$/day and most preferably less than 300 g/m$^2$/day. The intermediate coating layer acts as a binder or "glue" to bind the outer coating layer to the innermost coating layer.

The composition may optionally further comprise an additional humidity barrier coating layer, layered on the outer coating layer, for preventing further humidity penetration. If present, this additional humidity barrier coating layer is layered over the outer coating layer.

The composition may optionally further comprise an enteric polymer, layered on the humidity barrier coating layer, which may further provide protection against such destructive characteristics of the gastrointestinal tract as low pH values and proteolytic enzymes. The enteric polymer optionally comprises at least one plasticizer selected from the group consisting of polyethylene glycol (PEG), triethyl citrate and triacetin.

It should be noted that by "layering" it is meant any suitable process for adding the coating layer to the composition including but not limited to spraying, dipping, sprinkling and the like. Upon the addition of the layers to the core composition, particles are formed with three, four or more coating layers.

Optionally the following combination of ingredients may be applied as a non-limiting example: the at least one sugar may comprise, lactose, galactose or a mixture thereof, said at least one oligosaccharide or polysaccharides may comprise, galactan, maltodextrin, and trehalose, said stabilizer comprises L-cysteine base, said surfactant comprises tween 80 (polysorbate 80, Polyoxyethylene (20) sorbitan monooleate), said filler comprises lactose DC and/or microcrystalline cellulose, said binder comprises hydroxypropylmethylcelluloses, said hydrophobic solid fat or fatty acid comprises lauric acid and/or cacao butter said inner coating layer may comprise lauric acid and/or cacao butter, said intermediate coating layer polymer may comprise alginic acid or sodium alginate, said outer coating layer comprises carboxymethylcellulose (CMC) 7LFPH and/or carboxymethylcellulose (CMC) 7L2P, said plasticizer is polyethylene glycol (PEG) 400 and/or triacetin and said exterior coating layer comprises hydroxypropyl cellulose.

According to another non-limiting embodiment of the present invention, there is provided another process of manufacturing probiotic bacteria in a stabilized composition as follows. First, the core material is prepared as a mixture, with probiotic bacteria, a stabilizer, at least one sugar and at least one oligosaccharide, and optionally other food grade additives such as fillers, surfactant, binders, antioxidant, and etc., thereby obtaining a core mixture.

The core mixture is then wet granulated using a binder solution in purified water, or purified water under either air or nitrogen environment; alternatively, the core mixture is prepared using a hot melt granulation by using melt of a hydrophobic solid fat or fatty acid having a melting point below 50° C. In any case, the granulation process results in granulated core particles.

The particles of said core composition are coated with an inner coating layer comprising a hydrophobic solid fat or fatty acid for preventing or reducing the penetration of water or humidity into said core, thereby obtaining water sealed coated particles.

The water sealed coated particles are coated with an intermediate coating layer for adjusting surface tension thereby obtaining water sealed coated particles having an adjusted surface tension.

The water sealed coated particles having an adjusted surface tension are coated with an outer coating layer for reducing transmission of oxygen and humidity into the core obtaining oxygen and humidity sealed coated particles.

The oxygen and humidity sealed coated particles are coated with an exterior coating layer for reducing transmission of humidity into the core, thereby obtaining a multiple-layered particle containing probiotics showing superior stability against oxygen and humidity, and hence having higher viability and vitality.

Granulation as described herein may optionally be performed with fluidized bed technology such as Glatt or a Glatt turbo jet, or an Innojet coater/granulator, or a Huttlin coater/granulator, or a Granulex.

In any case the resulting probiotic composition according to the above processes may optionally be introduced to a food product which may also undergo a heating step during its preparation process. Alternatively the above resulting probiotic composition can be added to a food product which may not undergo a heating step during its preparation process.

Example 1

Preparation and Testing of an Exemplary Formulation

Preparation of an exemplary, illustrative formulation, described herein as Formula I, was performed as described below. Tests performed on Formula I are also described below.

For the preparation of Formula I, trehalose dihydrate 160 g, Maltodextrin DE15 314 g, L-Cystein-HCl Monohydrate 6 g and the bacteria BB12 (*Bifidobacteria*-BB12) 120 g were loaded into Innojet ventilus machine to receive a dry blend. Lauric acid 270 g was melted at 50° C. using a heating plate while stirring. Then hot melt of lauric acid was sprayed onto the above dry blend under an inert atmosphere using nitrogen. The temperatures of pump head, liquid, and spray pressure were set at 60° C. Core particles were therefore formed, based on a hot melt granulation process.

Next, the various layers were coated over the core particles as follows. For the first (innermost) layer, lauric acid 315 g was melted at 50° C. using a heating plate while stirring. Then hot melt of lauric acid was sprayed onto the above granulates under an inert atmosphere using nitrogen and such spraying parameters to obtain a film coat as a first sealing layer. Then Na-alginate (25.2 g) solution (2% w/w in purified water) was sprayed onto the above resulting granules (400 g) to obtain Na-alginate coated granules. 320 g of the above resulting Na-alginate coated granules were reloaded into the Innojet ventilus machine and additional portion of Na-alginate (58.97 g) solution (2% w/w in purified water) was sprayed to obtain finally 16.4% W/W Na-alginate in the formulation. Then 290 g of the above resulting Na-alginate coated granules were reloaded into the Innojet ventilus machine and the aqueous solution (5% w/w) of Na-carboxy methyl cellulose (Na-CMC) (72.92 g) and 19.98 g polyethylene glycol (PEG 400) (PEG 400/Na-CMC, 20% w/w) was sprayed onto the above resulting Na-alginate coated granules to obtain Na-CMC coated granules. Then 250 g of the above resulting Na-CMC coated granules were reloaded into the Innojet ventilus machine and additional portion of aqueous solution (5% w/w) of Na-CMC (61.70 g) and 15.4 g PEG 400 (PEG 400/Na-CMC, 20% w/w) was sprayed to obtain finally 29.32% W/W Na-CMC+PEG 400 in the final product.

The final product, particles of Formula I, was dried and kept in a double sealed polyethylene bag with a proper desiccant under refrigeration. It should be noted that various samples were taken from the above stages of preparation and were tested as described below.

Colony Forming Units Total Count Testing Method for Encapsulated *Bifidobacteria*-BB12 in Formula I The following testing method was used for the determination of colony forming units-total count (CFU) for encapsulated *Bifidobacteria*-BB12, prepared in Formula I as described above. This method is based on the dissolution of the coating layers of the encapsulated probiotics to liberate the probiotics prior to performing CFU test.

In this procedure both hydration and dissolution processes are applied to the coated particles, simulating the gastrointestinal tract and hence simulating the effect of ingesting the coated particles. As a result, the free bacterial cells are released. A medium that incorporates various selective agents is used to aid in the recovery of specific species and incubation in anaerobic conditions for increased recovery of the organisms. This method uses MRS agar with the additive Cysteine Hydrochloride as an oxygen scavenger.

The samples were plated in duplicates and average counts are reported (CFU/g).

The equipment included a sterile sampling device; 0.45 Micron Filtration Unit; Colony counter; Sterile Petri Dishes; Sterile pipettes; Incubator 37 +/−2° C.; Water bath 45 +/−2° C. for media tempering; Gaspak Anaerobic System: jar, or plastic chamber, anaerobic packets, and anaerobic indicator; Autoclave; Mortar and pestle; Stomacher; Analytical Balance; and Microscope slides.

Media:

The following media and reagents were used: MRS Broth, Difco #288130 (500 g); MRS Agar, Bacto Agar #21401 (484 g); L-Cysteine Hydrochloride, J.T.baker # G121-05; Tween-85 (Polyoxyethylene sorbitan trioleate), Sigma # P4634 (500 mL); Butterfield's Buffered Phosphate Diluent (BUT) MB 101.

MRS Broth (55 g/L) was prepared as follows. In a 1000 ml flask, the following ingredients were placed and mixed: 500 ml deionized water; 27.5 grams of dehydrated MRS Broth; 1 ml Tween-80 (polysorbate 80, Polyoxyethylene (20) sorbitan monooleate) (before sterilization). The broth was adjusted to a pH of 6.5+/−0.2 at 25° C.

MRS Agar (70 g/L) was prepared as follows. In a 1000 ml flask: the following ingredients were placed and mixed: 500 ml deionized water; 35 grams of dehydrated MRS Broth, followed by adjustment of the pH to 6.5+/−0.2 @ 25° C. Filter Sterilized L-Cysteine was added to the agar after sterilization.

MRS: Composition of MRS Agar (Purchased ready to use from Difco 288210 or equivalents):

| | |
|---|---|
| Polypeptone | 10 g/l |
| Meat Extract | 10 g/l |
| Yeast Extract | 5 g/l |
| Dextrose | 20 g/l |
| Tween 80 (polysorbate 80, Polyoxyethylene (20) sorbitan monooleate) | 1.0 g/l |
| Dipotassium phosphate | 2 g/l |
| Sodium acetate | 5 g/l |
| Ammonium citrate | 2 g/l |
| Magnesium sulfate | 0.1 g/l |
| Manganese sulfate | 0.05 g/l |
| Bacteriological Agar | 15 g/l |

Cysteine Hydrochloride (10% Solution) was prepared as follows. 10 grams of L-Cysteine was added to a clean 200 ml flask, with deionized water added to reach 100 ml volume. The L-cysteine was dissolved and filter sterilized using a 0.45 micron filtration unit.

The following procedure was used to test the protective effect of the composition of Formula I, to protect bacteria during storage and simulated release in the gastrointestinal tract, and to deliver live, viable bacteria to the site of colonization in the intestine. As used below, the term "sample" refers to the composition of Formula I.

About 20 g of the sample was crushed using a mortar and pestle for about 120 seconds, until the sample was homogeneously and finely crushed. 10 gram of the prepared crushed probiotic sample was placed into a sterile stomacher bag. 99 mL of warm phosphate buffer was added to the bag, warmed in the water-bath at 48° C.

The powder was dissolved uniformly and was then placed for 15 min (hydration time) in incubator (37° C.). Next, 2 mL of Tween 85 (Polyoxyethylene sorbitan trioleate) in hydrated mixture was added. The bag was kept in the water bath for 2 minutes, followed by application of the stomacher at 250 RPM for 2 min and incubation again in the water bath for 1 min. The stomacher was again applied at 250 RPM for 1 min. The resultant solution was serially diluted.

1 ml from appropriate dilutions was plated on appropriately labeled sterile Petri plates, followed by pouring MRS agar at a temperature of about 48° C. For each 100 ml of MRS agar, 0.5 mL of filter sterilized 10% L-Cysteine Hydrochloride was added before pouring. Plates were prepared in duplicate.

The plates were incubated anaerobically at 37° C. for 48-72 hours, followed by colony counting.

The following quantitative procedures were followed to count the colonies.

Colonies were counted on the MRS-cysteine plates, after selecting for those plates having 25-400 colonies, and the number was recorded as the Probiotic viable cell count per gram (CFU/g), taking into account the dilution factor of the plate counted. The counts from each plate were averaged at a given dilution for the total viable count per gram (i.e. CFU/g).

Results

The results of the test from different stages of the process for preparing the composition of Formula I are shown as CFU/g in the following table, Table 4.

TABLE 4

Probiotic bacteria viability after various stages of preparation

| Sample | CFU/g |
|---|---|
| Hot melt granulate of BB12 | $1.42 \times 10$ exp 13 |
| Na- alginate coated granulate of BB12 | $2.19 \times 10$ exp 13 |
| CMC coated granulate of BB12 | $5.42 \times 10$ exp 12- $1.29 \times 10$ exp 13 |

As can be seen from these results, fully coated particles provided the best protection to the bacteria, albeit with some variability in the results.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A composition comprising probiotic bacteria, the composition comprising:
    (a) a core composition containing the probiotic bacteria and a stabilizer, wherein the total amount of probiotics in the mixture is from about 10% to about 90% by weight of the core composition;
    (b) an innermost coating layer, layered on said core composition, comprising at least one hydrophobic solid fat, fatty acid or a wax having a melting point lower than 60° C., or a combination thereof;
    (c) an intermediate coating layer layered on said innermost coating layer, which when present in an aqueous solution in the amount of 0.1% weight/weight, has a surface tension lower than 60 mN/m, when measured at 25° C.; and
    (d) an outer coating layer, layered on said intermediate coating layer comprising low molecular weight carboxymethylcellulose having a molecular weight of 49,000-90,500 and a degree of substitution of 0.7;
    wherein the composition is in the form of particles.

2. The composition of claim 1, wherein said stabilizer comprises an oxygen scavenger wherein said oxygen scavenger comprises one or more of L-cysteine hydrochloride, L-cysteine base, 4,4 (2,3 dimethyl tetramethylene dipyrocatechol), tocopherol-rich extract (natural vitamin E), α-tocopherol (synthetic Vitamin E), β-tocopherol, γ-tocopherol, δ-tocopherol, butylhydroxinon, butyl hydroxyanisole (BHA), butyl hydroxytoluene (BHT), propyl gallate, octyl gallate, dodecyl gallate, tertiary butylhydroquinone (TBHQ) fumaric acid, malic acid, ascorbic acid (Vitamin C), sodium ascorbate, ascorbate, potassium ascorbate, ascorbyl palmitate, or ascorbyl stearate.

3. The composition of claim 1, wherein said stabilizer comprises a material selected from the group consisting of dipotassium edetate, disodium edetate, edetate calcium disodium, edetic acid, fumaric acid, malic acid, maltol, sodium edetate, and trisodium edetate.

4. The composition of claim 1, wherein said core composition further comprises at least one sugar compound, wherein said at least one sugar compound comprises one or more of a monosaccharide, a disaccharide, a trisaccharide, a tetrasaccharide, a higher oligosaccharide, or a polysaccharide, or a combination thereof; wherein said monosaccharide comprises one or more of ketotriose (dihydroxyacetone), aldotriose (glyceraldehyde), ketotetrose (erythrulose), erythrose, threose, ribulose, xylulose, ribose, arabinose, xylose, lyxose, deoxyribose, psicose, fructose, sorbose, tagatose, allose, altrose, glucose, mannose, gulose, idose, galactose, talose, fucose, fuculose, rhamnose, sedoheptulose, or neuraminic acid, or a combination thereof; wherein said disaccharide comprises one or more of sucrose, lactose, maltose, trehalose, turanose, or cellobiose, or a combination thereof; wherein said trisaccharide comprises one or more of raffinose, melezitose or maltotriose, or a combination thereof; wherein said tetrasaccharide comprises one or more of acarbose or stachyose, or a combination thereof; wherein said higher oligosaccharide comprises one or more of fructooligosaccharide (FOS), galactooligosaccharides (GOS) or mannan-oligosaccharides (MOS), or a combination thereof; wherein said polysaccharide comprises one or more of glucose-based polysaccharides/glucan cellulose, dextrin, dextran, beta-glucan, maltodextrin, fructose-based polysaccharides/fructan, levan beta 2-6, mannose-based polysaccharides, galactose-based polysaccharides, N-acetylglucosamine-based polysaccharides, or a gum, or a combination thereof; or wherein said polysaccharide comprises one or more of amylose, amylopectin, zymosan, lentinan, sizofiran, inulin, mannan, galactan, chitin, arabic gum, or gum acacia, or a combination thereof.

5. The composition of claim 1, wherein said core further comprises one or more of a filler, a surfactant or binder, or a combination thereof; wherein said filler comprises one or more of microcrystalline cellulose, a sugar; dicalcium phosphate; sugar alcohols, hydrogenated starch hydrolysates; corn starch; and potato starch; and/or a mixture thereof; wherein said binder comprises one or more of Povidone (PVP: polyvinyl pyrrolidone), Copovidone (copolymer of vinyl pyrrolidone and vinyl acetate), polyvinyl alcohol, low molecular weight HPC (hydroxypropyl cellulose), low molecular weight HPMC (hydroxypropyl methylcellulose), low molecular weight hydroxymethyl cellulose (MC), low molecular weight sodium carboxymethyl cellulose, low molecular weight hydroxyethyl cellulose, low molecular weight hydroxymethyl cellulose, cellulose acetate, gelatin, hydrolyzed gelatin, polyethylene oxide, acacia, dextrin, starch, water soluble polyacrylates and/or polymethacrylates, low molecular weight ethylcellulose, hydrophobic solid fat or fatty acid or a wax or a polyethylene glycol having a melting point lower than 60° C. or a mixture thereof; or wherein said surfactant comprises tween 80 (polysorbate 80, Polyoxyethylene (20) sorbitan monooleate), tween 20 (polysorbate 20, Polyoxyethylene (20) sorbitan monolaurate), tween 85 (Polyoxyethylene sorbitan trioleate) glycereth-2-cocoate, glycereth-6-cocoate, glycereth-7-cocoate, glycereth-17-cocoate or a mixture thereof.

6. The composition of claim 1, wherein said probiotic bacteria comprises one or more of *Bacillus coagulans* GBI-30, 6086, *Bacillus subtilis* var *natt*, *Bifidobacterium*, *Bifidobacterium* sp, *Bifidobacterium bifidum*, *Bifidobacterium bifidum* rosell-71, *Bifidobacterium breve*, *Bifidobacterium breve* Rosell-70, *Bifidobacterium infantis*, *Bifidobacterium lactis*, *Bifidobacterium longum*, *Bifidobacterium longum* Rosell-I 75, *Bifidobacterium animalis*, *Bifidobacterium animalis* subsp. *lactis* BB-12, *Bifidobacterium animalis* subsp. *lactis* HNO1 9, *Bifidobacterium infantis* 35624, *Escherichia coli* M-17, *Escherichia coli* Nissie 1917, *Lactobacillus acidophilus*, *Lactobacillus acidophilus*, *Lactobacillus acidophilus* LAFTI LI 0, *Lactobacillus casei*, *Lactobacillus casei* LAFTI L26, *Lactobacillus brevis*, *Lactobacillus bulgaricus*, *Lactobacillus casei*, *Lactobacillus gasseri*, *Lactobacillus paracasei*, *Lactobacillus plantarum*, *Lactobacillus reuteri* ATTC 55730 (*Lactobacillus reuteri* SD2112), *Lactobacillus rhamnosus*, *Lactobacillus salivarius*, *Lactobacillus delbrueckii*, *Lactobacillus fermentum*, *Lactococcus lactis*, *Lactococcus lactis* subsp, *Lactococcus lactis* Rosell-I 058, *Lactobacillus paracasei* Stl 1 (or NCC2461 *J Lactobacillus fortis* Nestle, *Lactobacillus johnsonii* La1 (=*Lactobacillus LCJ, Lactobacillus johnsonii* NCC533) Nestle, *Lactobacillus rhamnosus* Rosell-11, *Lactobacillus acidophilus* Rosell-52, *Streptococcus thermophilus*, *Diacetylactis*, *Saccharomyces cerevisiae*, and a mixture thereof.

7. The composition of claim 1, wherein said innermost coating layer comprises at least one hydrophobic solid fat or fatty acid having a melting point lower than 50° C.

8. The composition of claim 7, wherein said melting point is higher than 25° C.

9. The composition of claim 7, wherein said innermost coating layer comprises fatty acids, fatty acid esters, fatty acid triesters; aluminum, sodium, potassium and magnesium salts of fatty acids; fatty alcohols, phospholipids, solid fats, waxes, or a combination thereof.

10. The composition of claim 9, wherein the innermost coating layer comprises a solid fat comprising one or more of lauric acid, hydrogenated coconut oil, cacao butter or a combination thereof.

11. The composition of claim 1, wherein said innermost coating layer forms a stable hydrophobic matrix which embeds the core composition within and/or forms a film around the probiotic core composition; and optionally wherein said core comprises a plurality of cores and said plurality of cores is embedded in said stable hydrophobic matrix.

12. The composition of claim 1, wherein said intermediate coating layer, when present in an aqueous solution in the amount of 0.1% weight/weight, has a surface tension lower than 50 mN/m when measured at 25° C.

13. The composition of claim 12, wherein said intermediate coating layer comprises a polymer, comprising one or more of Hyroxypropylmethyl cellulose (HPMC), Hydroxypropylethyl cellulose (HPEC), Hydroxypropyl cellulose (HPC), hydroxypropylethyl cellulose (HPEC), hydroxymethylpropyl cellulose (HMPC), ethylhydroxyethyl cellulose (EHEC) (Ethulose), hydroxyethylmethyl cellulose (HEMC), hydroxymethylethyl cellulose (HMEC), propylhydroxyethyl cellulose (PHEC), methylhydroxyethyl cellulose (MHEC), hydrophobically modified hydroxyethyl cellulose, carboxymethylhydroxyethyl cellulose (CMHEC), Methyl cellulose, Ethyl cellulose, water soluble vinyl acetate copolymers, gums, polysaccharides such as alginic acid and alginates such as ammonia alginate, sodium alginate, potassium alginate, acid phthalate of carbohydrates, amylose acetate phthalate, cellulose acetate phthalate (CAP), cellulose ester phthalates, cellulose ether phthalates, hydroxypropyl cellulose phthalate (HPCP), hydroxypropylethyl cellulose phthalate (HPECP), hydroxyproplymethyl cellulose phthalate (HPMCP), hydroxyproplymethyl cellulose acetate succinate (HPMCAS), methyl cellulose phthalate (MCP), polyvinyl acetate phthalate (PVAcP), polyvinyl acetate hydrogen phthalate, sodium CAP, starch acid phthalate, cellulose acetate trimellitate (CAT), styrene-maleic acid dibutyl phthalate copolymer, styrene-maleic acid/polyvinylacetate phthalate copolymer, styrene and maleic acid copolymers, or polyacrylic acid derivatives or a combination thereof.

14. The composition of claim 13, wherein said polymer comprises one or more of shellac, phthalate derivatives, CAT, HPMCAS, polyacrylic acid derivatives, copolymers comprising acrylic acid and at least one acrylic acid ester, (poly(methacrylic acid, methyl methacrylate)1:2); (poly(methacrylic acid, methyl methacrylate)1:1); (poly(methacrylic acid, ethyl acrylate) 1:1); and (poly(methacrylic acid, ethyl acrylate) 1:1) an anionic polymer synthesized from methacrylic acid and methacrylic acid methyl ester), polymethyl methacrylate blended with acrylic acid and acrylic ester copolymers, alginic acid, ammonia alginate, sodium, potassium, magnesium or calcium alginate, vinyl acetate copolymers, polyvinyl acetate 30D (30% dispersion m water), a neutral methacrylic ester comprising poly(dimethylaminoethylacrylate), a copolymer of methylmethacrylate and ethylacrylate with trimethylammonioethyl methacrylate chloride, a copolymer of methylmethacrylate and ethylacrylate, Zein, shellac, gums, or polysaccharides, or a combination thereof.

\* \* \* \* \*